United States Patent
Sakamoto

(10) Patent No.: US 10,256,413 B2
(45) Date of Patent: Apr. 9, 2019

(54) MATERIAL FOR ORGANIC ELECTROLUMINESCENT DEVICE, ORGANIC ELECTROLUMINESCENT DEVICE INCLUDING THE SAME AND PREPARATION METHOD OF TRIARYLAMINE DERIVATIVES

(71) Applicant: SAMSUNG DISPLAY CO., LTD., Yongin-si, Gyeonggi-do (KR)

(72) Inventor: Naoya Sakamoto, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 147 days.

(21) Appl. No.: 15/048,505

(22) Filed: Feb. 19, 2016

(65) Prior Publication Data
US 2016/0315267 A1 Oct. 27, 2016

(30) Foreign Application Priority Data
Apr. 21, 2015 (JP) ................................. 2015-086493

(51) Int. Cl.
*H01L 51/00* (2006.01)
*C07D 307/91* (2006.01)
(Continued)

(52) U.S. Cl.
CPC ........ *H01L 51/0061* (2013.01); *C07D 307/91* (2013.01); *C07D 333/76* (2013.01);
(Continued)

(58) Field of Classification Search
None
See application file for complete search history.

(56) References Cited

U.S. PATENT DOCUMENTS

2007/0196691 A1* 8/2007 Ikemizu .............. C07F 15/0033
428/690
2007/0228941 A1* 10/2007 Abe ...................... C07C 211/54
313/504

FOREIGN PATENT DOCUMENTS

JP 5040216 B2 10/2012
JP 5742092 B2 7/2015
(Continued)

OTHER PUBLICATIONS

Abstract of Japanese Publication No. 2007091719 A, Apr. 12, 2007 Corresponding to Japanese Patent No. 5040216 B2, Oct. 3, 2012, 1 Page.
(Continued)

Primary Examiner — Eli S Mekhlin
(74) Attorney, Agent, or Firm — Lewis Roca Rothgerber Christie LLP

(57) ABSTRACT

Provided are a material for an organic electroluminescent device having a high emission efficiency and an organic electroluminescent device including the same. The material for an organic electroluminescent device according to the present disclosure is represented by Formula 1:

Formula 1

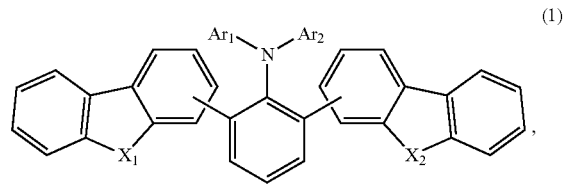

in which dibenzoheterole groups are coupled to a phenyl group of a triarylamine at the ortho positions relative to the
(Continued)

nitrogen atom. The polarity of the molecule may be increased due to the heteroatoms of the dibenzoheterole groups, and the energy gap (e.g., HOMO-LUMO gap) of the molecule may be increased due to the large steric distortion of the molecule around the amine group. Accordingly, the emission efficiency of an organic EL device may be improved in the blue emission region.

1 Claim, 1 Drawing Sheet

(51) Int. Cl.
 *C07D 333/76* (2006.01)
 *C07D 409/10* (2006.01)
 *H01L 51/50* (2006.01)
(52) U.S. Cl.
 CPC ........ *C07D 409/10* (2013.01); *H01L 51/0052* (2013.01); *H01L 51/0059* (2013.01); *H01L 51/0073* (2013.01); *H01L 51/0074* (2013.01); *H01L 51/5056* (2013.01)

(56) References Cited

FOREIGN PATENT DOCUMENTS

| WO | WO 2014/104515 A1 | 7/2014 | |
|---|---|---|---|
| WO | WO 2014/146752 A1 | 9/2014 | |
| WO | WO 2016105138 A2 * | 6/2016 | ........... C07D 403/10 |
| WO | WO-2016105138 A2 * | 6/2016 | ........... C07D 403/10 |

OTHER PUBLICATIONS

Abstract of Japanese Publication No. 2011051936 A, Mar. 17, 2011 Corresponding to Japanese Patent No. 5742092 B2, Jul. 1, 2015, 2, Pages.

\* cited by examiner

MATERIAL FOR ORGANIC ELECTROLUMINESCENT DEVICE, ORGANIC ELECTROLUMINESCENT DEVICE INCLUDING THE SAME AND PREPARATION METHOD OF TRIARYLAMINE DERIVATIVES

CROSS-REFERENCE TO RELATED APPLICATION

This U.S. patent application claims priority to and the benefit of Japanese Patent Application No. 2015-086493, filed on Apr. 21, 2015, in the Japan Patent Office, the entire content of which is incorporated herein by reference.

BACKGROUND

1. Field

One or more aspects of embodiments of the present disclosure relate to a material for an organic electroluminescent device, an organic electroluminescent device using the same, a method of preparing triarylamine derivatives, a hole transport material for an organic electroluminescent device having high emission efficiency and long life, an organic electroluminescent device using the same, and/or a preparation method of the material for an organic electroluminescent device.

2. Description of the Related Art

Organic electroluminescent (EL) displays are currently being actively developed. Unlike liquid crystal displays, etc., organic EL displays are so-called self-luminescent displays that function by recombining holes and electrons from an anode and a cathode in an emission layer to generate excitons for emitting light energy. Light is emitted from a luminescent organic compound in the emission layer.

An example organic EL device includes an anode, a hole transport layer on the anode, an emission layer on the hole transport layer, an electron transport layer on the emission layer, and a cathode on the electron transport layer. Holes injected from the anode move via the hole transport layer to the emission layer. Electrons injected from the cathode move via the electron transport layer to the emission layer. When the holes and electrons injected into the emission layer are recombined, excitons are generated in the emission layer. The organic EL device emits light using energy generated by the radiative decay of the excitons. Configurations of the organic EL device are not limited to the above example, and may be diversely modified.

When organic EL devices are used in display apparatuses, the organic EL devices should exhibit high emission efficiencies and long lifetimes. However, driving voltages are high and emission efficiencies are insufficient in many organic EL devices, for example, those in the blue emission region. Methods of increasing the normalization, stabilization, and durability of the hole transport layer have been examined as strategies for increasing the efficiencies and lifetimes of organic EL devices.

Many aromatic amine compounds are available as hole transport materials for use in a hole transport layer. For example, an amine derivative substituted with a heteroaryl ring has been suggested as a useful material for increasing the emission efficiency of an organic EL device in the blue emission region. However, issues related to resolving the emission efficiency of the device remain, and it is difficult to say that an organic EL device using the material has a sufficient emission efficiency. For example, the emission efficiencies of organic EL devices are low in the blue emission region relative to the red and green emission regions, and an increase of emission efficiency in the blue emission region is desirable. An aniline derivative having aryl groups at positions 2 and 6 has been suggested as a material for increasing the emission efficiency of an organic EL device; however, a device using the material was not considered to have sufficient emission efficiency. An aniline derivative having substituents at positions 2 and 6 has been disclosed as a luminescent material but was considered to be inappropriate or unsuitable as a hole transport material, because the amine site is a ring shape (e.g., contained within a cyclic moiety) and the compound includes an electron withdrawing group. Accordingly, further developments on material for an organic EL device having an even higher efficiency are needed.

SUMMARY

One or more aspects of embodiments of the present disclosure are directed toward a material for an organic EL device having a high emission efficiency, an organic EL device including the same, and a method of preparing the material for an organic EL device.

One or more embodiments of the present disclosure also provide a material for an organic EL device having a high emission efficiency in the blue emission region, an organic EL device including the same in at least one laminated layer, and a method of preparing the material for an organic EL device.

An embodiment of the present disclosure provides a material for an organic EL device represented by the following Formula 1:

Formula 1

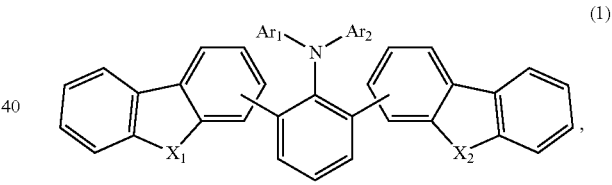

In Formula 1, $Ar_1$ and $Ar_2$ may each independently be selected from a substituted or unsubstituted aryl group having 6 to 30 carbon atoms for forming a ring, and a substituted or unsubstituted heteroaryl group having 1 to 30 carbon atoms for forming a ring. $X_1$ and $X_2$ may each independently be selected from O, S, $R_1$—Si—$R_2$ and N—$R_3$, and $R_1$ to $R_3$ may each independently be selected from an alkyl group having 1 to 10 carbon atoms, and an aryl group having 6 to 30 carbon atoms for forming a ring.

The material for an organic EL device according to an embodiment of the present disclosure may include an aniline derivative having a structure in which dibenzoheterole groups are introduced (e.g., coupled) to a phenyl group of a triarylamine at the ortho positions relative to the nitrogen atom. The polarity of the molecule may be increased due to the heteroatoms of the dibenzoheterole groups, and the energy gap (e.g., HOMO-LUMO gap) of the molecule may be increased due to the large steric distortion of the molecule around the amine group. Accordingly, the emission efficiency of an organic EL device may be improved in the blue emission region.

In Formula 1, $X_1$ and $X_2$ may each independently be selected from O and S.

In an embodiment of the present disclosure, $Ar_1$ and $Ar_2$ in Formula 1 may each independently be selected from a naphthyl group, a biphenyl group, a terphenyl group, a naphthylphenyl group, a dibenzofuryl group and a dibenzothiophenyl group.

In an embodiment of the present disclosure, an organic EL device includes an anode, an emission layer on the anode, and a laminated layer between the anode and the emission layer. At least one selected from the emission layer and the laminated layer may include a material for an organic EL device represented by Formula 1:

Formula 1

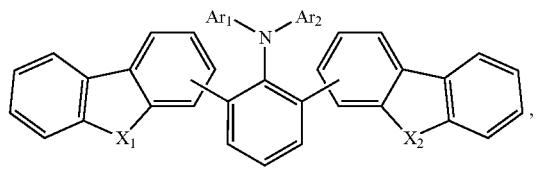
(1)

In Formula 1, $Ar_1$ and $Ar_2$ may each independently be selected from a substituted or unsubstituted aryl group having 6 to 30 carbon atoms for forming a ring and a substituted or unsubstituted heteroaryl group having 1 to 30 carbon atoms for forming a ring; $X_1$ and $X_2$ may each independently be selected from O, S, $R_1$—Si—$R_2$ and N—$R_3$, and $R_1$ to $R_3$ may each independently be selected from an alkyl group having 1 to 10 carbon atoms and an aryl group having 6 to 30 carbon atoms for forming a ring.

In an embodiment of the present disclosure, the laminated layer may include a hole transport layer, and the hole transport layer may include the material for an organic EL device.

The organic EL device according to an embodiment of the present disclosure may attain a high emission efficiency by including one of the materials for an organic EL device in at least one of the laminated layers between the emission layer and the anode (for example, as a material for a hole transport layer).

In an embodiment of the present disclosure, a method of preparing a triarylamine derivative represented by the following Formula 1 includes preparing an amine derivative by reacting a 1-amino-2,6-halogenated benzene with a dibenzoheterole derivative substituted with boronic acid, and reacting the resulting primary amine derivative with an unsubstituted aryl halide group having 6 to 30 carbon atoms for forming a ring or a substituted or unsubstituted heteroaryl halide group having 1 to 30 carbon atoms for forming a ring.

Formula 1

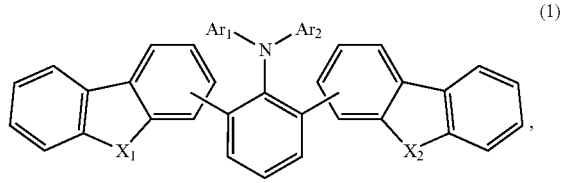
(1)

In Formula 1, $Ar_1$ and $Ar_2$ may each independently be selected from a substituted or unsubstituted aryl group having 6 to 30 carbon atoms for forming a ring, and a substituted or unsubstituted heteroaryl group having 1 to 30 carbon atoms for forming a ring; $X_1$ and $X_2$ may each independently be selected from O, S, $R_1$—Si—$R_2$ and N—$R_3$; and $R_1$ to $R_3$ may each independently be selected from an alkyl group having 1 to 10 carbon atoms, and an aryl group having 6 to 30 carbon atoms for forming a ring.

BRIEF DESCRIPTION OF THE DRAWINGS

The accompanying drawings are included to enable further understanding of the present disclosure, and are incorporated in and constitute a part of this specification. The drawings illustrate example embodiments of the present disclosure and, together with the description, serve to explain principles of the present disclosure. In the drawings.

DETAILED DESCRIPTION

Figure 1:
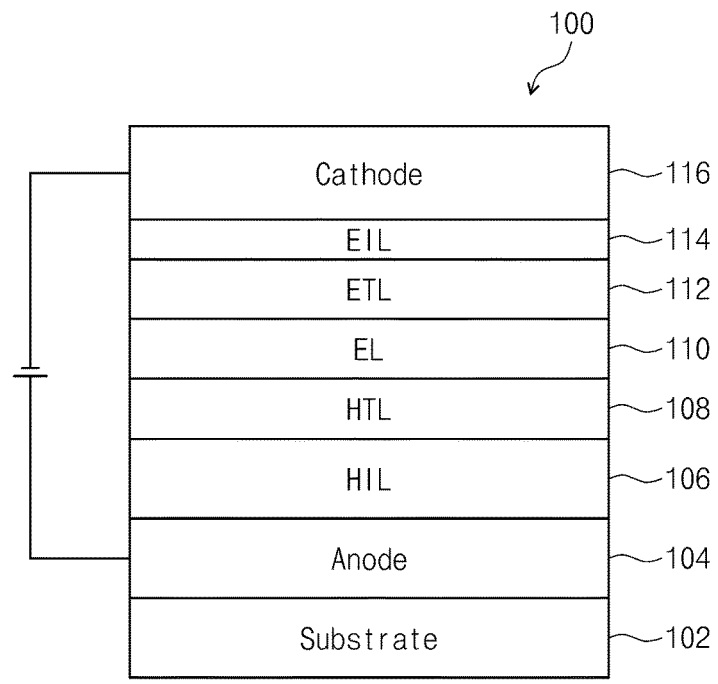
FIG. 1 is a schematic diagram of an organic EL device 100 according to an embodiment of the present disclosure.

Hereinafter, the material for an organic EL device and the organic EL device including the same according to an embodiment of the present disclosure will be described with reference to the accompanying drawings. The material for an organic EL device and the organic EL device including the same may, however, be embodied in different forms and should not be construed as limited to the embodiments set forth herein. In the drawings, like reference numerals refer to like elements or elements having like functions throughout, and repeated explanations thereof will not be provided.

In the drawings, the thicknesses of layers, films, panels, regions, etc., may be exaggerated for clarity. It will be understood that when an element such as a layer, film, region, or substrate is referred to as being "on" another element, it can be directly on the other element or intervening element(s) may also be present. In contrast, when an element is referred to as being "directly on" another element, no intervening elements are present.

One or more embodiments of the present disclosure provide a material for an organic EL device including an amine compound, represented by the following Formula 1:

Formula 1

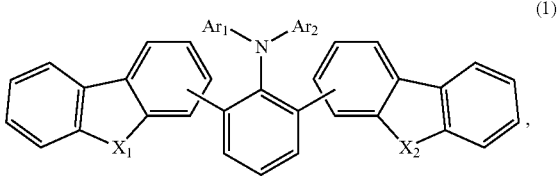
(1)

In Formula 1, $Ar_1$ and $Ar_2$ may each independently be selected from a substituted or unsubstituted aryl group having 6 to 30 carbon atoms for forming a ring and a substituted or unsubstituted heteroaryl group having 1 to 30 carbon atoms for forming a ring. $X_1$ and $X_2$ may each independently be selected from 0, S, and N—$R_3$, and $R_1$ to $R_3$ may each independently be selected from an alkyl group having 1 to 10 carbon atoms and an aryl group having 6 to 30 carbon atoms for forming a ring. As used herein, "atoms for forming a ring" may refer to "ring-forming atoms".

In Formula 1, non-limiting examples of the aryl group having 6 to 30 carbon atoms for forming a ring used as $Ar_1$ and Ar$_2$ may include a phenyl group, a naphthyl group, an anthracenyl group, a phenanthryl group, a biphenyl group, a terphenyl group, a quaterphenyl group, a fluorenyl group, a triphenylenyl group, a pyrenyl group, a benzofluoranthenyl group, a chrysenyl group, a phenylnaphthyl group, a naphthylphenyl group, etc. In some embodiments, the aryl group may have 10 to 18 carbon atoms for forming a ring and may be selected from a naphthyl group, a biphenyl group, a terphenyl group, and a naphthylphenyl group.

Non-limiting examples of the heteroaryl group having 1 to 30 carbon atoms for forming a ring used as Ar$_1$ and Ar$_2$ may include a benzothiazolyl group, a thiophenyl group, a thienothiophenyl group, a dithienothiophenyl group, a benzothiophenyl group, a benzofuryl group, a dibenzothiophenyl group, a dibenzofuryl group, an N-arylcarbazolyl group, an N-heteroarylcarbazolyl group, an N-alkylcarbazolyl group, a phenoxazyl group, a phenothiazyl group, a pyridyl group, a pyrimidyl group, a triazyl group, a quinolinyl group, a quinoxalyl group, etc. In some embodiments, Ar$_1$ and Ar$_2$ may be a heteroaryl group having 12 to 18 carbon atoms for forming a ring, and non-limiting examples may include the dibenzofuryl group and the dibenzothiophenyl group.

Ar$_1$ and Ar$_2$ may include one or more substituents selected from an alkyl group, an alkoxy group having 1 to 6 carbon atoms, and a phenyl group. Non-limiting examples of the alkyl group having 1 to 6 carbon atoms may include a methyl group, an ethyl group, an n-propyl group, an i-propyl group, an n-butyl group, an s-butyl group, a t-butyl group, an n-pentyl group, an n-hexyl group, a c-propyl group, a c-butyl group, a c-pentyl group, a c-hexyl group, etc. Non-limiting examples of the alkoxy group having 1 to 6 carbon atoms may include a methoxy group, an ethoxy group, an n-propoxy group, an i-propoxy group, an n-butoxy group, an s-butoxy group, a t-butoxy group, an n-pentoxy group, an n-hexoxy group, a c-propoxy group, a c-butoxy group, a c-pentoxy group, a c-hexoxy group, etc.

As described above, in Formula 1, X$_1$ and X$_2$ may each independently be selected from O, S, R$_1$—Si—R$_2$, and N—R$_3$, and R$_1$ to R$_3$ may each independently be selected from an alkyl group having 1 to 10 carbon atoms and an aryl group having 6 to 30 carbon atoms for forming a ring. In some embodiments, X$_1$ and X$_2$ may each independently be selected from O and S.

Non-limiting examples of the alkyl group having 1 to 10 carbon atoms used as R$_1$ to R$_3$ may include a methyl group, an ethyl group, an n-propyl group, an i-propyl group, an n-butyl group, an s-butyl group, a t-butyl group, an n-pentyl group, an n-hexyl group, a c-propyl group, a c-butyl group, a c-pentyl group, a c-hexyl group, etc. Non-limiting examples of the alkoxy group having 1 to 6 carbon atoms may include a methoxy group, an ethoxy group, an n-propoxy group, an i-propoxy group, an n-butoxy group, an s-butoxy group, a t-butoxy group, an n-pentoxy group, an n-hexoxy group, a c-propoxy group, a c-butoxy group, a c-pentoxy group, a c-hexoxy group, etc.

Non-limiting examples of the aryl group having 6 to 30 carbon atoms for forming a ring used as R$_1$ to R$_3$ may include a phenyl group, a naphthyl group, an anthracenyl group, a phenanthryl group, a biphenyl group, a terphenyl group, a quaterphenyl group, a fluorenyl group, a triphenylenyl group, a pyrenyl group, a benzofluoranthenyl group, a chrysenyl group, a phenylnaphthyl group, a naphthylphenyl group, etc.

The material for an organic EL device according to an embodiment of the present disclosure may be an aniline derivative having a structure in which dibenzoheterole groups are introduced (e.g., coupled) to a phenyl group of a triarylamine at the ortho positions relative to the nitrogen atom. The polarity of the molecules may be increased due to the heteroatoms of the dibenzoheterole groups, and the energy gap (e.g., HOMO-LUMO gap) of the molecule may be increased due to the large steric distortion of the molecule near the amine. Accordingly, the emission efficiency of an organic EL device may be improved. When the material for an organic EL device according to an embodiment of the present disclosure is included in at least one laminated layer between the emission layer and the anode in an organic EL device (for example, as a material for a hole transport layer), the emission efficiency of the organic EL device may be improved in the blue emission region.

The material for an organic EL device according to an embodiment of the present disclosure may be one selected from the following Compounds (2) to (23), in which Compounds (2)-(19) are collectively referred to as Formula 2, and Compounds (20)-(23) are collectively referred to as Formula 3.

Formula 2

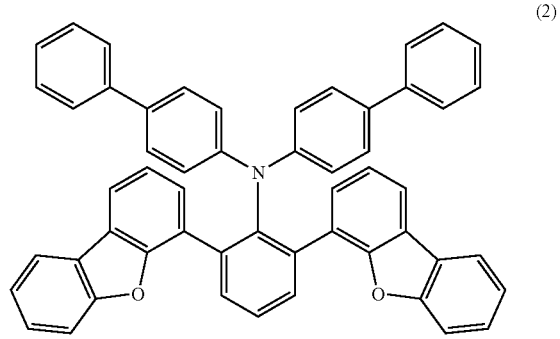

(2)

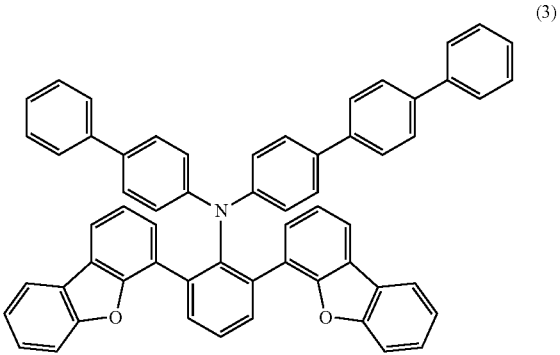

(3)

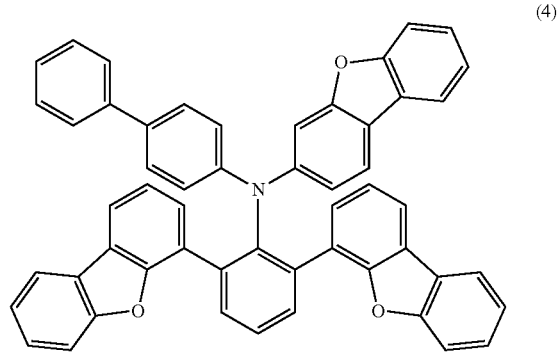

(4)

(5)
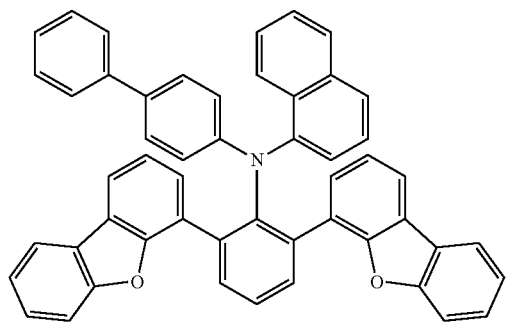
(9)
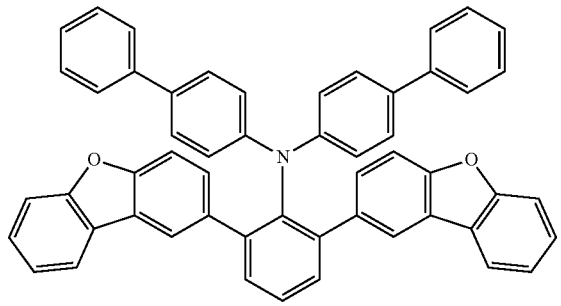
(6)
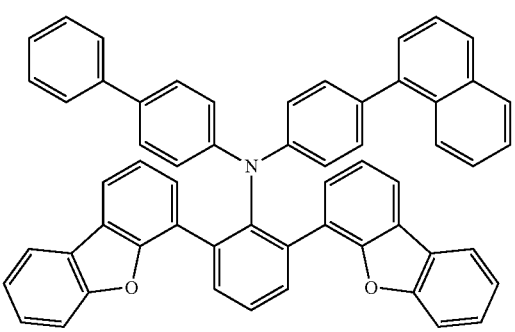
(10)
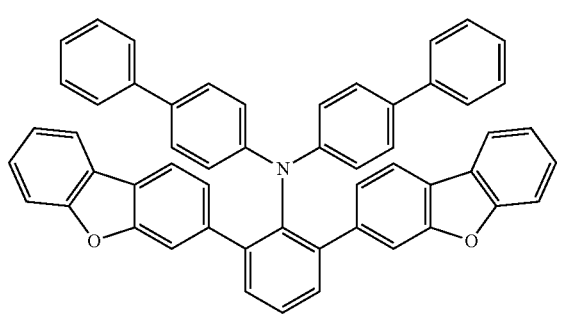
(7)
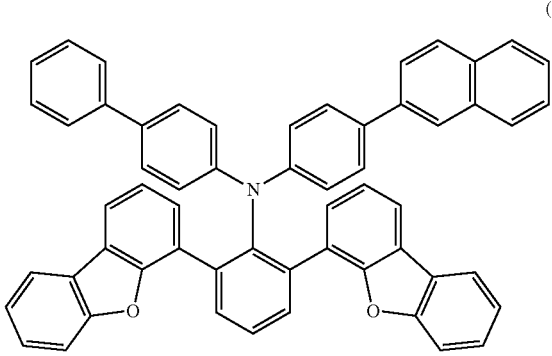
(11)
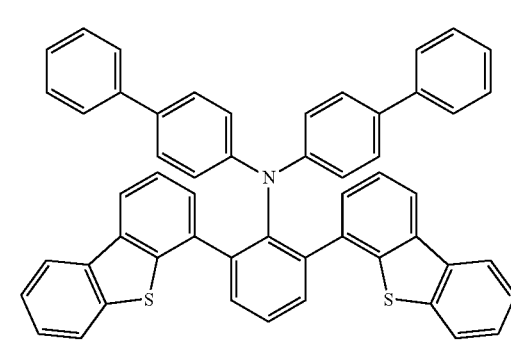
(8)
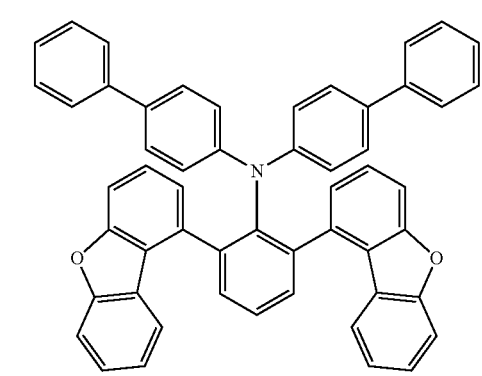
(12)
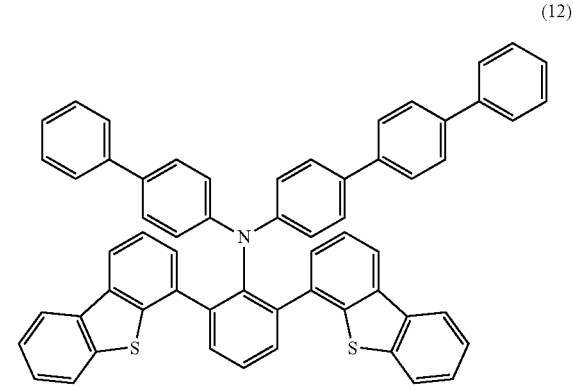

(13)
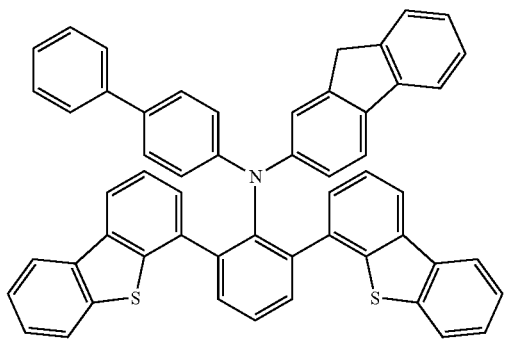
(14)
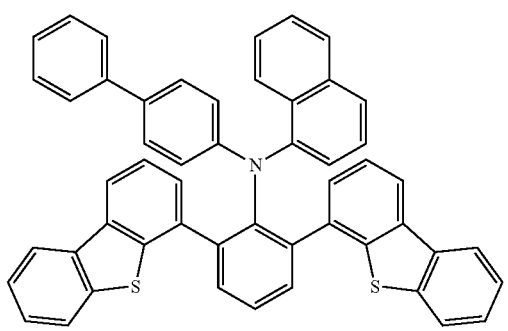
(15)
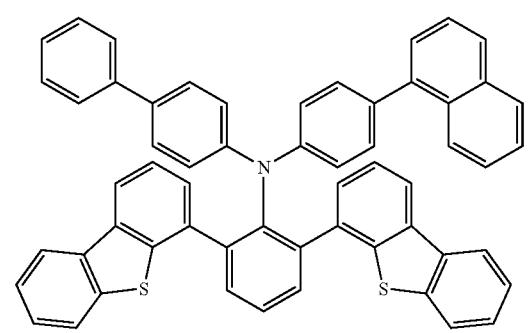
(16)
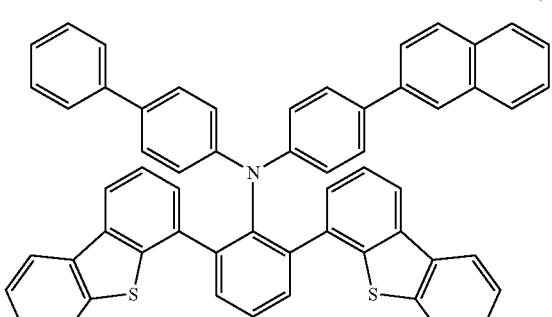
(17)
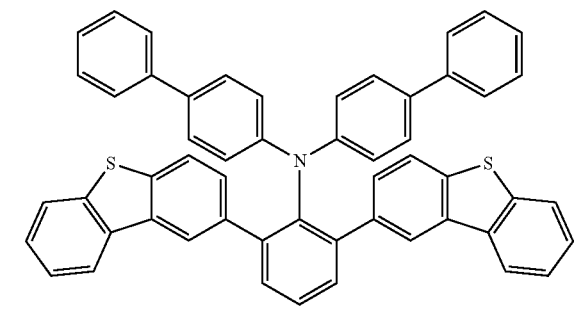
(18)
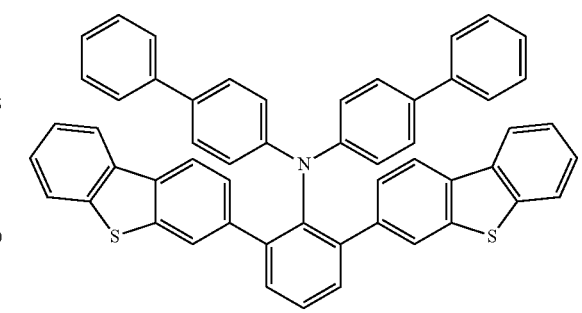
(19)
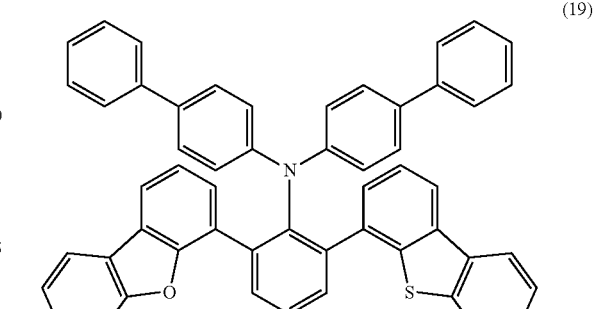
Formula 3
(20)
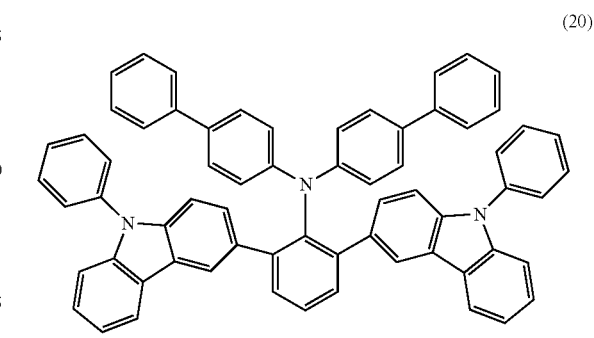

(21)

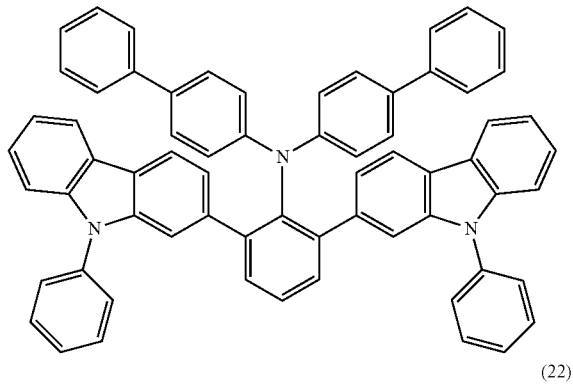

(22)

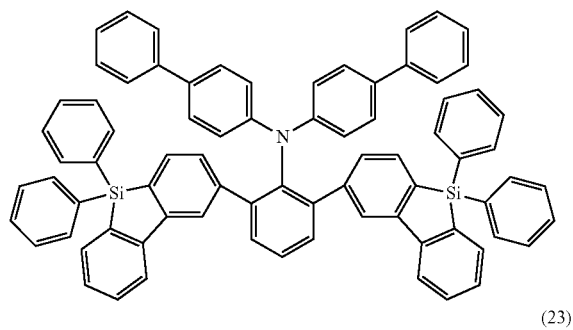

(23)

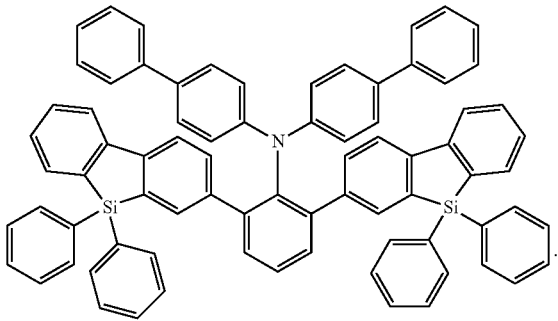

The material for an organic EL device according to an embodiment of the present disclosure may be included in at least one layer selected from a plurality of organic layers forming an organic EL device. For example, the material may be included in at least one laminated layer between an emission layer and an anode in the organic EL device.

As described above, the material for an organic EL device according to an embodiment of the present disclosure may be an aniline derivative having a structure in which dibenzoheterole groups are introduced (e.g., coupled) to a phenyl group of a triarylamine at the ortho positions relative to the nitrogen atom. In the material for an organic EL device according to an embodiment of the present disclosure, the polarity of the molecule may be increased due to the heteroatoms of the dibenzoheterole groups, and the energy gap (e.g., HOMO-LUMO gap) of the molecule may be increased due to the large steric distortion of the molecule around the amine group, thereby improving the emission efficiency of the organic EL device.

The material for an organic EL device according to an embodiment of the present disclosure is not limited to being used as the material included in a layer between an emission layer and an anode in an organic EL device, but may also be used as the material of the emission layer. When the material for an organic EL device according to an embodiment of the present disclosure is used as a material for a hole transport layer, the emission efficiency of the organic EL device may be improved in the blue emission region.

Organic EL Device

Hereinafter, an organic EL device using a material for an organic EL device according to an embodiment of the present disclosure will be explained. FIG. 1 is a schematic diagram illustrating an organic EL device 100 according to an embodiment of the present disclosure. The organic EL device 100 may include, for example, a substrate 102, an anode 104, a hole injection layer 106, a hole transport layer 108, an emission layer 110, an electron transport layer 112, an electron injection layer 114 and a cathode 116. The material for an organic EL device according to an embodiment of the present disclosure may be used in at least one laminated layer between the emission layer and the anode.

An embodiment where the material for an organic EL device according to the present disclosure is used in the hole transport layer 108 will be explained in more detail.

The substrate 102 may be a transparent glass substrate, a semiconductor substrate formed using silicon, and/or a flexible substrate made of a resin, etc.

The anode 104 may be on the substrate 102 and may be formed using indium tin oxide (ITO), indium zinc oxide (IZO), etc.

The hole injection layer (HIL) 106 may be formed on the anode 104 to a thickness of about 10 nm to about 150 nm using any suitable material. The material may include, for example, triphenylamine-containing polyether ketone (TPA-PEK), 4-isopropyl-4'-methyldiphenyliodonium tetrakis(pentaflorophenyl)borate (PPBI), N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4''-tris(3-methylphenylphenylamino) triphenylamine (m-MTDATA), N,N'-di(1-naphthyl)-N,N'-diphenylbenzidine (NPB), 4,4',4''-tris{N,N-diphenylamino}triphenylamine (TDATA), 4,4',4''-tris(N,N-2-naphthylphenylamino)triphenylamine (2-TNATA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), etc.

The hole transport layer (HTL) 108 may be formed on the hole injection layer 106 to a thickness of about 10 nm to about 150 nm using the material for an organic EL device according to an embodiment of the present disclosure. In the case where the material for an organic EL device according to an embodiment of the present disclosure is used as a material for the emission layer (EL) 110, the hole transport layer 108 may be formed using any suitable hole transport material. The hole transport material may include, for example, 1,1-bis[(di-4-tolylamino)phenyl]cyclohexane (TAPC), a carbazole derivative such as N-phenylcarbazole and polyvinyl carbazole, N,N'-bis(3-methylphenyl)-N,N'-diphenyl-[1,1-biphenyl]-4,4'-diamine (TPD), 4,4',4''-tris(N-carbazolyl triphenylamine (TCTA), N,N'-di(1-naphthyl)-N,N'-diphenylbenzidine (NPB), etc. In some embodiments, the hole transport material and the material for an organic EL device according to an embodiment of the present disclosure may be combined and used to form the hole transport layer 108.

The emission layer (EL) 110 may be formed on the hole transport layer 108 to a thickness of about 10 nm to about 60 nm using any suitable host material. Non-limiting examples of the host material used in the emission layer 110 may include tris(8-quinolinolato)aluminum (Alq3), 4,4'-N,N'-dicarbazole-biphenyl (CBP), poly(N-vinylcarbazole) (PVK), 9,10-di(naphthalene-2-yl)anthracene (ADN), 4,4',4''-tris(N-carbazolyl)triphenylamine (TCTA), (1,3,5-tris(N-phenyl-benzimidazole)-2-yl)benzene (TPBI), 3-tert-butyl-9,10-di (naphth-2-yl)anthracene (TBADN), distyrylarylene (DSA), 4,4'-bis(9-carbazole)-2,2'-dimethyl-biphenyl (dmCBP), etc.

The dopant material of the emission layer 110 may include styryl derivatives (such as 1,4-bis[2-(3-N-ethylcarbazolyl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-yl)vinyl) phenyl-N-phenylbenzeneamine) (N-BDAVBi), perylene and derivatives thereof (such as 2,5,8,11-tetra-t-butylperylene (TBPe)), pyrene and derivatives thereof (such as 1,1-dipyrene, 1,4-dipyrenylbenzene, and 1,4-bis(N,N-diphenylamino)pyrene), etc. However, the type or kind of dopant is not limited thereto.

The electron transport layer (ETL) 112 may be formed to a thickness of about 15 nm to about 50 nm on the emission layer 110 using, for example, tris(8-hydroxyquinolinolato) aluminum (Alq3) and/or a material having a nitrogen-containing aromatic ring (for example, a material including a pyridine ring such as 1,3,5-tri[(3-pyridyl)-phen-3-yl]benzene, a material including a triazine ring such as 2,4,6-tris (3'-(pyridin-3-yl)biphenyl-3-yl)1,3,5-triazine, and a material including an imidazole derivative such as 2-(4-N-phenyl-benzoimidazolyl-1-ylphenyl)-9,10-dinaphthylanthracene).

The electron injection layer (EIL) 114 may be formed to a thickness of about 0.3 nm to about 9 nm on the electron transport layer 112 using, for example, a material including lithium fluoride (LiF), lithium-8-quinolinato (LiQ), etc.

The cathode 116 may be on the electron injection layer 114 and may be formed using a metal (such as aluminum (Al), silver (Ag), lithium (Li), magnesium (Mg) and/or calcium (Ca)) and/or a transparent material (such as ITO and/or IZO).

Each electrode and layer forming the organic EL device according to an embodiment of the present disclosure may be formed using an appropriate or suitable layer forming method according to the material to be used, such as a vacuum evaporation method, a sputtering method, and other coating methods available in the art.

The efficiency of the organic EL device 100 may be increased by including the material for an organic EL device according to an embodiment of the present disclosure in the hole transport layer.

In the organic EL device 100 according to an embodiment of the present disclosure, the material for an organic EL device may be used as a material for a hole injection layer or a material for the host material of an emission layer. As described above, the efficiency of an organic EL device may be improved by including the material for an organic EL device in at least one layer selected from a plurality of organic layers forming the organic EL device.

The material for an organic EL device according to an embodiment of the present disclosure may be applied to an active matrix type (e.g., active matrix) organic EL display using thin film transistors (TFTs). Hereinafter, a method of synthesizing a triarylamine derivative of Formula 1 will be explained in more detail according to example embodiments.

General Synthetic Method of Triarylamine Derivative

In the synthetic method of a triarylamine derivative as the material for an organic EL device according to an embodiment of the present disclosure, a primary amine derivative may be produced by reacting a 1-amino-2,6-halogenated benzene with a dibenzofuran derivative, a dibenzothiophene derivative, a dibenzosilole derivative, and/or a carbazole derivative substituted with boronic acid in the presence of a catalyst and optional additives. Then, a triarylamine derivative represented by the following Formula 1 may be prepared by reacting the primary amine derivative with an unsubstituted aryl halide group having 6 to 30 carbon atoms for forming a ring or a substituted or unsubstituted heteroaryl halide group having 1 to 30 carbon atoms for forming a ring in the presence of a catalyst, a base, and optional additives. The reaction yield of the 1-diarylamino-2,6-halogenated benzene and the dibenzoheterole derivative substituted with boronic acid may be very low (e.g., low) due to the steric hindrance of the diarylamino group.

Formula 1

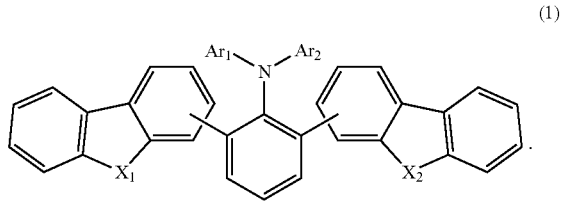

(1)

In Formula 1, $Ar_1$ and $Ar_2$ may each independently be selected from a substituted or unsubstituted aryl group having 6 to 30 carbon atoms for forming a ring and a substituted or unsubstituted heteroaryl group having 1 to 30 carbon atoms for forming a ring; $X_1$ and $X_2$ may each independently be selected from O, S, $R_1$—Si—$R_2$ and N—$R_3$; and $R_1$ to $R_3$ may each independently be selected from an alkyl group having 1 to 10 carbon atoms and an aryl group having 6 to 30 carbon atoms for forming a ring.

Non-limiting examples of the 1-amino-2,6-halogenated benzene may include 2,6-dichloroaniline, 2,6-dibromoaniline, 2,6-diiodoaniline, 2-bromo-6-iodoaniline, etc.

Non-limiting examples of the dibenzofuran derivative substituted with boronic acid may include, for example, dibenzofuran-1-boronic acid, dibenzofuran-2-boronic acid, dibenzofuran-3-boronic acid, dibenzofuran-4-boronic acid, etc.

Non-limiting examples of the dibenzothiophene derivative substituted with boronic acid may include dibenzothiophene-2-boronic acid, dibenzothiophene-3-boronic acid, dibenzothiophene-4-boronic acid, etc.

Non-limiting examples of the dibenzosilole derivative substituted with boronic acid may include 9,9-dimethyl-9-silafluorene-2-boronic acid, 9,9-dimethyl-9-silafluorene-3-boronic acid, 9,9-diethyl-9-silafluorene-2-boronic acid, 9,9-diethyl-9-silafluorene-3-boronic acid, 9,9-diphenyl-silafluorene-2-boronic acid, 9,9-diphenyl-9-silafluorene-3-boronic acid, etc.

Non-limiting examples of the carbazole derivative substituted with boronic acid may include 9-methylcarbazolyl-2-boronic acid, 9-methylcarbazolyl-3-boronic acid, 9-ethylcarbazolyl-2-boronic acid, 9-ethylcarbazolyl-3-boronic acid, 9-phenylcarbazolyl-2-boronic acid, 9-phenylcarbazolyl-3-boronic acid, etc.

Non-limiting examples of the solvent used in the reaction of the 1-amino-2,6-halogenated benzene with the dibenzofuran derivative, the dibenzothiophene derivative, the dibenzosilole derivative, and/or the carbazole derivative substituted with boronic acid to prepare the amine derivative may include toluene, dimethoxyethane, tetrahydrofuran, acetone, acetonitrile, 1,4-dioxane, and mixtures thereof with water. Non-limiting examples of a catalyst for the coupling reaction may include tetrakis(triphenylphosphine)palladium(0), palladium(II) acetate, bis(triphenylphosphine)palladium(II) dichloride, [1,1'-bis(diphenylphosphino)ferrocene]palladium(II)dichloride dichloromethane adduct, dichloro(1,5-cyclooctadiene)palladium(II), [1,1'-bis(di-tert-butylphosphino)ferrocene]palladium(II) dichloride, etc., and non-limiting examples of a base may include sodium carbonate, potassium carbonate, rubidium carbonate, cesium carbonate, tripotassium phosphate, etc. Non-limiting examples of optional additives may include triphenylphosphine, 2-dicyclohexylphosphino-2',6'-bimethoxybiphenyl (SPhos), 2-dicyclohexylphosphino-2',4',6'-triisopropylbiphenyl (XPhos), etc.

Non-limiting examples of the unsubstituted aryl halide group having 6 to 30 carbon atoms for forming a ring may include dibromobenzene, iodobenzene, 4-bromobiphenyl, 4-iodobiphenyl, 4-bromo-p-terphenyl, 1-bromonaphthalene, 2-bromonaphthalene, 1-iodonaphthalene, 2-iodonaphthalene, 1-(4-bromophenyl)naphthalene, 2-(4-bromophenyl)naphthalene, 2-bromoanthracene, 9-bromoanthracene, 2-bromophenanthrene, 9-bromophenanthrene, 2-bromotriphenylene, 1-bromopyrene, 2-bromopyrene, etc.

Non-limiting examples of the substituted or unsubstituted heteroaryl halide group having 1 to 30 carbon atoms for forming a ring may include 2-bromodibenzofuran, 3-bromodibenzofuran, 4-bromodibenzofuran, 2-bromodibenzothiophene, 3-bromodibenzothiophene, 4-bromodibenzothiophenen, 2-iododibenzofuran, 3-iododibenzofuran, 4-iododibenzofuran, 2-iododibenzothiophene, 3-iododibenzothiophene, 4-iododibenzothiophene, 2-bromo-9-phenylcarbazole, 2-bromo-9-methylcarbazole, 2-bromo-9-ethylcarbazole, 3-bromo-9-phenylcarbazole, 3-bromo-9-methylcarbazole, 3-bromo-9-ethylcarbazole, 2-bromopyridine, 3-bromopyridine, 4-bromopyridine, 2-iodopyridine, 3-iodopyridine, 4-iodopyridine, 2-bromoquinoline, 3-bromoquinoline, 4-bromoquinoline, 5-bromoquinoline, 6-bromoquinoline, 7-bromoquinoline, etc.

Non-limiting examples of the solvent used in the reaction of the primary amine derivative with the unsubstituted aryl halide group having 6 to 30 carbon atoms for forming a ring, and/or the substituted or unsubstituted heteroaryl halide group having 1 to 30 carbon atoms for forming a ring to prepare the triarylamine derivative represented by Formula 1 may include toluene, xylene, methylene, dimethylformamide, tetrahydrofuran, etc. Non-limiting examples of a catalyst for the coupling reaction may include bis(dibenzylideneacetone)palladium(0), [1,1'-bis(diphenylphosphino)ferrocene]palladium(II)dichloride dichloromethane adduct, tris(dibenzylideneacetone)dipalladium(0), palladium(II) acetate, etc., and non-limiting examples of a base may include sodium tert-butoxide, potassium tert-butoxide, n-butyllithium, etc. Non-limiting examples of optional additives may include tri-tert-butylphosphine, 2-dicyclohexylphosphino-2',6'-bimethoxybiphenyl, 2-dicyclohexylphosphino-2',4',6'-triisopropylbiphenyl, 2,2'-bis(diphenylphosphino)-1,1'-binaphthyl, etc.

Embodiment 1 of Synthetic Method of
Triarylamine Derivative

In the reaction of a 1-amino-2,6-halogenated benzene with a dibenzofuran derivative substituted with boronic acid to prepare a primary amine derivative, a mixture of toluene, water and ethanol is used as a solvent, tetrakis(triphenylphosphine)palladium(0) is used as a catalyst, and potassium carbonate is used as a base. In the reaction of the resulting primary amine derivative with an unsubstituted aryl halide group having 6 to 30 carbon atoms for forming a ring or a substituted or unsubstituted heteroaryl halide group having 1 to 30 carbon atoms for forming a ring, toluene is used as a solvent, bis(dibenzylideneacetone)palladium(0) is used as a catalyst, sodium tert-butoxide is used as a base, and tri-tert-butylphosphine is used as an additive.

Embodiment 2 of Synthetic Method of
Triarylamine Derivative

In the reaction of a 1-amino-2,6-halogenated benzene with a dibenzofuran derivative substituted with boronic acid to prepare a primary amine derivative, a mixture of toluene, water and ethanol is used as a solvent, tetrakis(triphenylphosphine)palladium(0) is used as a catalyst, and sodium carbonate is used as a base. In the reaction of the resulting primary amine derivative with an unsubstituted aryl halide group having 6 to 30 carbon atoms for forming a ring or a substituted or unsubstituted heteroaryl halide group having 1 to 30 carbon atoms for forming a ring, toluene is used as a solvent, bis(dibenzylideneacetone)palladium(0) is used as a catalyst, sodium tert-butoxide is used as a base, and tri-tert-butylphosphine is used as an additive.

Embodiment 3 of Synthetic Method of
Triarylamine Derivative

In the reaction of a 1-amino-2,6-halogenated benzene with a dibenzofuran derivative substituted with boronic acid to prepare a primary amine derivative, a mixture of toluene, water and ethanol is used as a solvent, tetrakis(triphenylphosphine)palladium(0) is used as a catalyst, and tripotassium phosphate is used as a base. In the reaction of the resulting primary amine derivative with an unsubstituted aryl halide group having 6 to 30 carbon atoms for forming a ring or a substituted or unsubstituted heteroaryl halide group having 1 to 30 carbon atoms for forming a ring, toluene is used as a solvent, bis(dibenzylideneacetone)palladium(0) is used as a catalyst, sodium tert-butoxide is used as a base, and tri-tert-butylphosphine is used as an additive.

Embodiment 4 of Synthetic Method of
Triarylamine Derivative

In the reaction of a 1-amino-2,6-halogenated benzene with a dibenzofuran derivative substituted with boronic acid to prepare a primary amine derivative, a mixture of toluene, water and ethanol is used as a solvent, palladium(II) acetate is used as a catalyst, tripotassium phosphate is used as a base, and SPhos is used as an additive. In the reaction of the resulting primary amine derivative with an unsubstituted aryl halide group having 6 to 30 carbon atoms for forming a ring or a substituted or unsubstituted heteroaryl halide group having 1 to 30 carbon atoms for forming a ring, toluene is used as a solvent, bis(dibenzylideneacetone)palladium(0) is used as a catalyst, sodium tert-butoxide is used as a base, and tri-tert-butylphosphine is used as an additive.

Embodiment 5 of Synthetic Method of
Triarylamine Derivative

In the reaction of a 1-amino-2,6-halogenated benzene with a dibenzofuran derivative substituted with boronic acid to prepare a primary amine derivative, a mixture of toluene, water and ethanol is used as a solvent, palladium(II) acetate is used as a catalyst, potassium carbonate is used as a base, and SPhos is used as an additive. In the reaction of the resulting primary amine derivative with an unsubstituted aryl halide group having 6 to 30 carbon atoms for forming a ring or a substituted or unsubstituted heteroaryl halide group having 1 to 30 carbon atoms for forming a ring, toluene is used as a solvent, bis(dibenzylideneacetone)palladium(0) is used as a catalyst, sodium tert-butoxide is used as a base, and tri-tert-butylphosphine is used as an additive.

Embodiment 6 of Synthetic Method of Triarylamine Derivative

In the reaction of a 1-amino-2,6-halogenated benzene with a dibenzofuran derivative substituted with boronic acid to prepare a primary amine derivative, a mixture solvent of toluene, water and ethanol is used as a solvent, palladium(II) acetate is used as a catalyst, sodium carbonate is used as a base, and SPhos is used as an additive. In the reaction of the resulting primary amine derivative with an unsubstituted aryl halide group having 6 to 30 carbon atoms for forming a ring or a substituted or unsubstituted heteroaryl halide group having 1 to 30 carbon atoms for forming a ring, toluene is used as a solvent, bis(dibenzylideneacetone)palladium(0) is used as a catalyst, sodium tert-butoxide is used as a base, and tri-tert-butylphosphine is used as an additive.

Embodiment 7 of Synthetic Method of Triarylamine Derivative

In the reaction of a 1-amino-2,6-halogenated benzene with a dibenzofuran derivative substituted with boronic acid to prepare a primary amine derivative, a mixture solvent of toluene, water and ethanol is used as a solvent, tetrakis(triphenylphosphine)palladium(0) is used as a catalyst, and cesium carbonate is used as a base. In the reaction of the primary amine derivative with an unsubstituted aryl halide group having 6 to 30 carbon atoms for forming a ring or a substituted or unsubstituted heteroaryl halide group having 1 to 30 carbon atoms for forming a ring, toluene is used as a solvent, bis(dibenzylideneacetone)palladium(0) is used as a catalyst, sodium tert-butoxide is used as a base, and tri-tert-butylphosphine is used as an additive.

Embodiment 8 of Synthetic Method of Triarylamine Derivative

In the reaction of a 1-amino-2,6-halogenated benzene with a dibenzofuran derivative substituted with boronic acid to prepare a primary amine derivative, a mixture of toluene, water and ethanol is used as a solvent, palladium(II) acetate is used as a catalyst, cesium carbonate is used as a base, and SPhos is used as an additive. In the reaction of the resulting primary amine derivative with an unsubstituted aryl halide group having 6 to 30 carbon atoms for forming a ring or a substituted or unsubstituted heteroaryl halide group having 1 to 30 carbon atoms for forming a ring, toluene is used as a solvent, bis(dibenzylideneacetone)palladium(0) is used as a catalyst, sodium tert-butoxide is used as a base, and tri-tert-butylphosphine is used as an additive.

Embodiment 9 of Synthetic Method of Triarylamine Derivative

In the reaction of a 1-amino-2,6-halogenated benzene with a dibenzofuran derivative substituted with boronic acid to prepare a primary amine derivative, a mixture of toluene, water and ethanol is used as a solvent, tetrakis(triphenylphosphine)palladium(0) is used as a catalyst, and potassium carbonate is used as a base. In the reaction of the resulting primary amine derivative with an unsubstituted aryl halide group having 6 to 30 carbon atoms for forming a ring or a substituted or unsubstituted heteroaryl halide group having 1 to 30 carbon atoms for forming a ring, toluene is used as a solvent, bis(dibenzylideneacetone)palladium(0) is used as a catalyst, n-butyllithium is used as a base, and tri-tert-butylphosphine is used as an additive.

Embodiment 10 of Synthetic Method of Triarylamine Derivative

In the reaction of a 1-amino-2,6-halogenated benzene with a dibenzofuran derivative substituted with boronic acid to prepare a primary amine derivative, a mixture solvent of toluene, water and ethanol is used as a solvent, tetrakis(triphenylphosphine)palladium(0) is used as a catalyst, and sodium carbonate is used as a base. In the reaction of the resulting primary amine derivative with an unsubstituted aryl halide group having 6 to 30 carbon atoms for forming a ring or a substituted or unsubstituted heteroaryl halide group having 1 to 30 carbon atoms for forming a ring, toluene is used as a solvent, bis(dibenzylideneacetone)palladium(0) is used as a catalyst, n-butyllithium is used as a base, and tri-tert-butylphosphine is used as an additive.

Embodiment 11 of Synthetic Method of Triarylamine Derivative

In the reaction of a 1-amino-2,6-halogenated benzene with a dibenzofuran derivative substituted with boronic acid to prepare a primary amine derivative, a mixture of toluene, water and ethanol is used as a solvent, tetrakis(triphenylphosphine)palladium(0) is used as a catalyst, and tripotassium phosphate is used as a base. In the reaction of the resulting primary amine derivative with an unsubstituted aryl halide group having 6 to 30 carbon atoms for forming a ring or a substituted or unsubstituted heteroaryl halide group having 1 to 30 carbon atoms for forming a ring, toluene is used as a solvent, bis(dibenzylideneacetone)palladium(0) is used as a catalyst, n-butyllithium is used as a base, and tri-tert-butylphosphine is used as an additive.

Embodiment 12 of Synthetic Method of Triarylamine Derivative

In the reaction of a 1-amino-2,6-halogenated benzene with a dibenzofuran derivative substituted with boronic acid to prepare a primary amine derivative, a mixture of toluene, water and ethanol is used as a solvent, palladium(II) acetate is used as a catalyst, tripotassium phosphate is used as a base, and SPhos is used as an additive. In the reaction of the resulting primary amine derivative with an unsubstituted aryl halide group having 6 to 30 carbon atoms for forming a ring or a substituted or unsubstituted heteroaryl halide group having 1 to 30 carbon atoms for forming a ring, toluene is used as a solvent, bis(dibenzylideneacetone)palladium(0) is used as a catalyst, n-butyllithium is used as a base, and tri-tert-butylphosphine is used as an additive.

Embodiment 13 of Synthetic Method of Triarylamine Derivative

In the reaction of a 1-amino-2,6-halogenated benzene with a dibenzofuran derivative substituted with boronic acid to prepare a primary amine derivative, a mixture of toluene, water and ethanol is used as a solvent, palladium(II) acetate is used as a catalyst, potassium carbonate is used as a base, and SPhos is used as an additive. In the reaction of the resulting primary amine derivative with an unsubstituted aryl halide group having 6 to 30 carbon atoms for forming a ring or a substituted or unsubstituted heteroaryl halide group having 1 to 30 carbon atoms for forming a ring, toluene is used as a solvent, bis(dibenzylideneacetone)palladium(0) is used as a catalyst, n-butyllithium is used as a base, and tri-tert-butylphosphine is used as an additive.

Embodiment 14 of Synthetic Method of Triarylamine Derivative

In the reaction of a 1-amino-2,6-halogenated benzene with a dibenzofuran derivative substituted with boronic acid to prepare a primary amine derivative, a mixture of toluene, water and ethanol is used as a solvent, palladium(II) acetate is used as a catalyst, sodium carbonate is used as a base, and SPhos is used as an additive. In the reaction of the resulting primary amine derivative with an unsubstituted aryl halide group having 6 to 30 carbon atoms for forming a ring or a substituted or unsubstituted heteroaryl halide group having 1 to 30 carbon atoms for forming a ring, toluene is used as a solvent, bis(dibenzylideneacetone)palladium(0) is used as a catalyst, n-butyllithium is used as a base, and tri-tert-butylphosphine is used as an additive.

Embodiment 15 of Synthetic Method of Triarylamine Derivative

In the reaction of a 1-amino-2,6-halogenated benzene with a dibenzofuran derivative substituted with boronic acid to prepare a primary amine derivative, a mixture of toluene, water and ethanol is used as a solvent, tetrakis(triphenylphosphine)palladium(0) is used as a catalyst, and cesium carbonate is used as a base. In the reaction of the resulting primary amine derivative with an unsubstituted aryl halide group having 6 to 30 carbon atoms for forming a ring or a substituted or unsubstituted heteroaryl halide group having 1 to 30 carbon atoms for forming a ring, toluene is used as a solvent, bis(dibenzylideneacetone)palladium(0) is used as a catalyst, n-butyllithium is used as a base, and tri-tert-butylphosphine is used as an additive.

Embodiment 16 of Synthetic Method of Triarylamine Derivative

In the reaction of a 1-amino-2,6-halogenated benzene with a dibenzofuran derivative substituted with boronic acid to prepare a primary amine derivative, a mixture of toluene, water and ethanol is used as a solvent, palladium(II) acetate is used as the catalyst, cesium carbonate is used as a base, and SPhos is used as an additive. In the reaction of the resulting primary amine derivative with an unsubstituted aryl halide group having 6 to 30 carbon atoms for forming a ring or a substituted or unsubstituted heteroaryl halide group having 1 to 30 carbon atoms for forming a ring, toluene is used as a solvent, bis(dibenzylideneacetone)palladium(0) is used as a catalyst, n-butyllithium is used as a base, and tri-tert-butylphosphine is used as an additive.

EXAMPLES

Synthetic Examples of Compounds

General Synthetic Method 1

Under an argon atmosphere, a boronic acid derivative, tetrakis(triphenylphosphine)palladium(0), and potassium carbonate were added to a 1-amino-2,6-halogenated benzene, followed by heating and stirring in a mixture solvent of toluene, water and ethanol (10:2:1) (controlling the concentration of the halogenated benzene at about 0.1 M) at about 80° C. for about 10 hours. After cooling, water was added, the organic phase was separated and dried with magnesium sulfate, and solvents were distilled. The crude product thus obtained was separated by silica gel column chromatography (toluene/hexane) to produce a purified product.

Synthesis of Compound A

Synthetic method 1 was conducted using 2,6-dibromoaniline (10.0 g), dibenzofuran-4-boronic acid (2 eq.), tetrakis(triphenylphosphine)palladium(0) (0.1 mol %) and potassium carbonate (4 eq.). 13.5 g of Compound A was produced (Yield: 80%). The molecular weight of the product thus obtained was measured by fast atom bombardment (FAB-MS) to be 425, and the chemical formula thereof was taken to be $C_{30}H_{19}NO_2$, corresponding to Compound A.

Formula 4

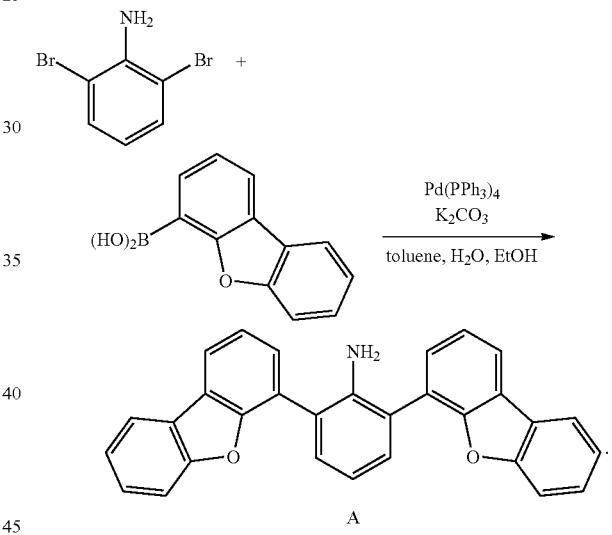

Synthesis of Compound B

Synthetic method 1 was conducted using 2,6-dibromoaniline (3.0 g), dibenzofuran-4-boronic acid (1 eq.), tetrakis(triphenylphosphine)palladium(0) (0.05 mol %) and potassium carbonate (2 eq.). 2.2 g of Compound B was produced (Yield: 55%). The molecular weight of the product thus obtained was measured by FAB-MS to be 337, and the chemical formula thereof was taken to be $C_{18}H_{12}BrNO$, corresponding to Compound B.

Formula 5

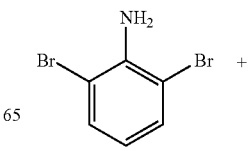

-continued

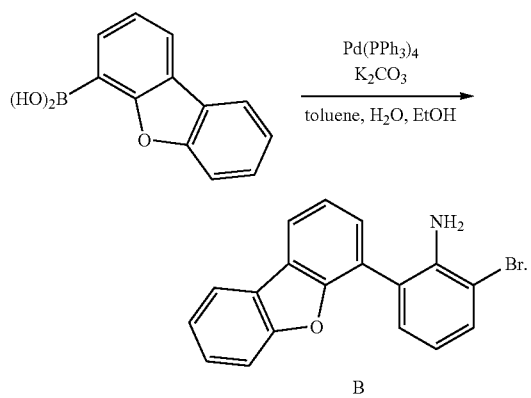

B

Synthesis of Compound C

Synthetic method 1 was conducted using 2,6-dibromoaniline (10.0 g), dibenzothiophene-4-boronic acid (2 eq.), tetrakis(triphenylphosphine)palladium(0) (0.1 mol %) and potassium carbonate (4 eq.). 13.5 g of Compound C was produced (Yield: 80%). The molecular weight of the product thus obtained was measured by FAB-MS to be 457, and the chemical formula thereof was taken to be $C_{30}H_{19}NS_2$, corresponding to Compound C.

Formula 6

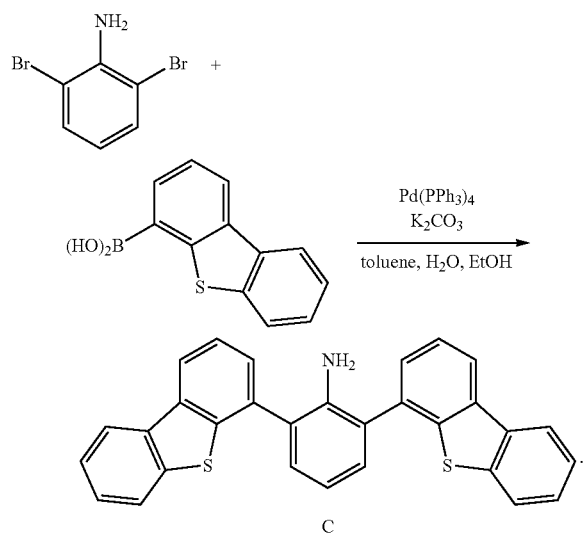

C

Synthesis of Compound D

Synthetic method 1 was conducted using Compound B (2.2 g), dibenzothiophene-4-boronic acid (1 eq.), tetrakis(triphenylphosphine)palladium(0) (0.05 mol %) and potassium carbonate (2 eq.). 2.3 g of Compound D was produced (Yield 83%). The molecular weight of the product thus obtained was measured by FAB-MS to be 441, and the chemical formula thereof was taken to be $C_{30}H_{19}NOS$, corresponding to Compound D.

Formula 7

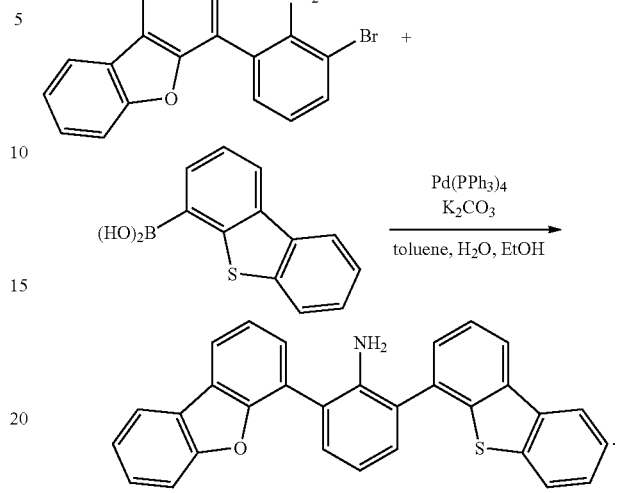

D

Synthetic Method 2

Under an argon atmosphere, an aryl halide or heteroaryl halide, bis(dibenzylideneacetone)palladium(0), tri-tert-butylphosphine, and sodium tert-butoxide were added to a primary amine derivative, followed by heating and refluxing in a toluene solvent (controlling the concentration of the primary amine derivative at about 0.1 M) for about 4 hours. After cooling, water was added, the organic phase was separated and dried with magnesium sulfate, and solvents were distilled. The crude product thus obtained was separated by silica gel column chromatography (toluene/hexane) to produce the purified target product.

Synthesis of Compound E

Synthetic method 2 was conducted using Compound A (10.0 g), 4-bromobiphenyl (1 eq.), bis(dibenzylideneacetone)palladium(0) (5 mol %), tri-tert-butylphosphine (20 mol %), and sodium tert-butoxide (1.5 eq.). 13.5 g of Compound E was produced (Yield: 80%). The molecular weight of the product thus obtained was measured by FAB-MS to be 577, and the chemical formula thereof was taken to be $C_{42}H_{27}NO_2$, corresponding to Compound E.

Formula 8

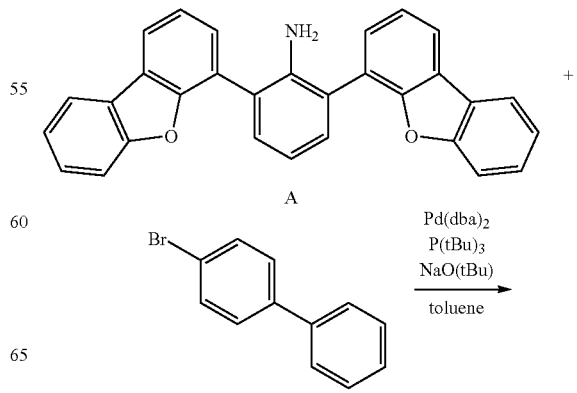

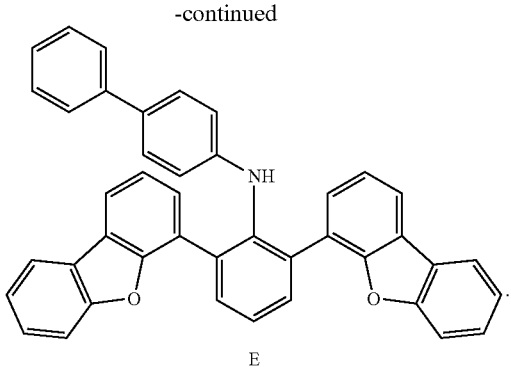

E

Synthesis of Compound 2

Synthetic method 2 was conducted using Compound A (2.0 g), 4-bromobiphenyl (2 eq.), bis(dibenzylideneacetone)palladium(0) (10 mol %), tri-tert-butylphosphine (40 mol %) and sodium tert-butoxide (3 eq.). 3.0 g of Compound 2 was produced (Yield: 88%). The molecular weight of the product thus obtained was measured by FAB-MS to be 729, and the chemical formula thereof was taken to be $C_{54}H_{35}NO_2$, corresponding to Compound 2.

Synthesis of Compound 4

Synthetic method 2 was conducted using Compound E (2.0 g), 3-bromodibenzofuran (1 eq.), bis(dibenzylideneacetone)palladium(0) (5 mol %), tri-tert-butylphosphine (20 mol %) and sodium tert-butoxide (1.5 eq.). 2.2 g of Compound 4 was produced (Yield: 86%). The molecular weight of the product thus obtained was measured by FAB-MS to be 743, and the chemical formula thereof was taken to be $C_{54}H_{33}NO_3$, corresponding to Compound 4.

Synthesis of Compound 6

Synthetic method 2 was conducted using Compound E (2.0 g), 1-(4-bromophenyl)naphthalene (1 eq.), bis(dibenzylideneacetone)palladium(0) (5 mol %), tri-tert-butylphosphine (20 mol %) and sodium tert-butoxide (1.5 eq.). 2.1 g of Compound 6 was produced (Yield 78%). The molecular weight of the product thus obtained was measured by FAB-MS to be 779, and the chemical formula thereof was taken to be $C_{58}H_{37}NO_2$, corresponding to Compound 6.

Synthesis of Compound 11

Synthetic method 2 was conducted using Compound C (2.0 g), 4-bromobiphenyl (2 eq.), bis(dibenzylideneacetone)palladium(0) (10 mol %), tri-tert-butylphosphine (40 mol %) and sodium tert-butoxide (3 eq.). 2.8 g of Compound 11 was produced (Yield: 84%). The molecular weight of the product thus obtained was measured by FAB-MS to be 761, and the chemical formula thereof was taken to be $C_{54}H_{35}NS_2$, corresponding to Compound 11.

Synthesis of Compound 19

Synthetic method 2 was conducted using Compound D (2.0 g), 4-bromobiphenyl (2 eq.), bis(dibenzylideneacetone)palladium(0) (10 mol %), tri-tert-butylphosphine (40 mol %) and sodium tert-butoxide (3 eq.). 3.0 g of Compound 19 was produced (Yield: 89%). The molecular weight of the product thus obtained was measured by FAB-MS to be 745, and the chemical formula thereof was taken to be $C_{54}H_{35}NOS$, corresponding to Compound 19.

Organic EL devices according to Examples 1 to 7 were manufactured using Compounds 2, 4, 6, 11 and 19 as hole transport materials (collectively referred to as Formula 9), synthesized by the above-described manufacturing methods.

Formula 9

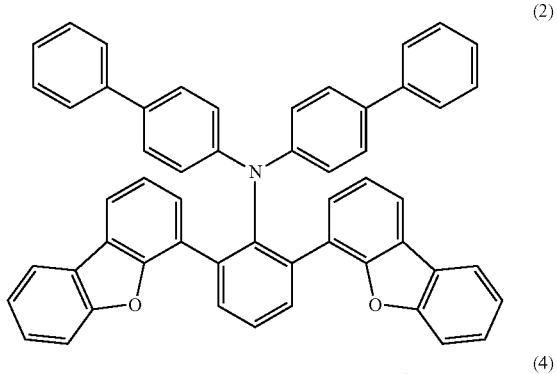

(2)

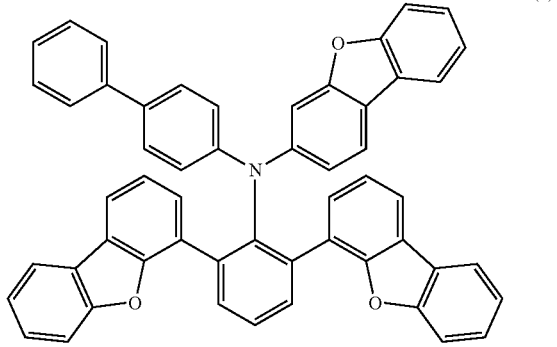

(4)

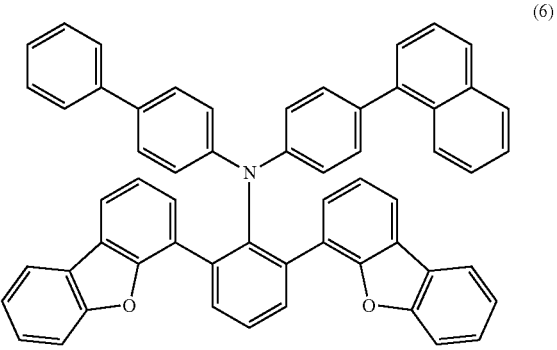

(6)

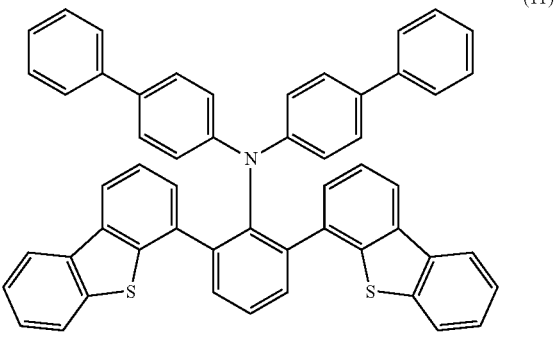

(11)

-continued (19)

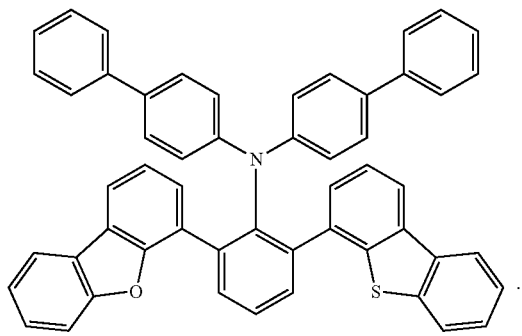

For comparison, organic EL devices according to Comparative Examples 1 and 2 were manufactured using the following Comparative Compounds C1 and C2 (collectively referred to as Formula 10) as hole transport materials.

Formula 10

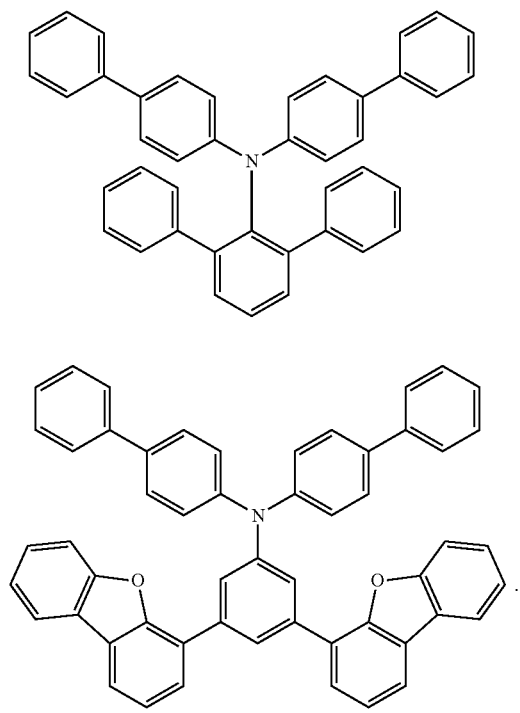

Figure 2:
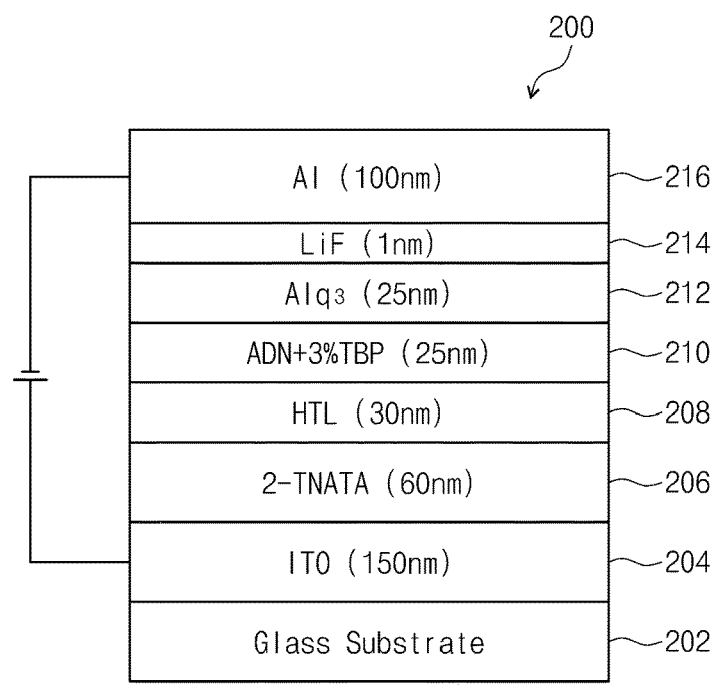
FIG. 2 is a schematic diagram of an organic EL device 200 according to another embodiment of the present disclosure.

An organic EL device 200 according to an embodiment of the present disclosure is shown in FIG. 2. In this embodiment, a substrate 202 was formed using a transparent glass substrate, and an anode 204 was formed using ITO to a thickness of about 150 nm. A hole injection layer 206 was formed using 2-TNATA to a thickness of about 60 nm, a hole transport layer 208 was formed to a thickness of about 30 nm, and an emission layer 210 was formed using ADN doped with 3% TBP to a thickness of about 25 nm. An electron transport layer 212 was formed using Alq3 to a thickness of about 25 nm, an electron injection layer 214 was formed using LiF to a thickness of about 1 nm, and a cathode 216 was formed using Al to a thickness of about 100 nm.

For the organic EL devices 200 thus manufactured, emission efficiencies were evaluated. The emission efficiencies were measured at a current density of 10 mA/cm$^2$. The evaluation results are shown in the following Table 1. The brightness light distribution characteristics measurement system of HAMAMATSU Photonics Co. was used in evaluating the emission properties of the organic EL devices.

TABLE 1

| Device manufacturing example | Hole transport layer | Emission efficiency |
| --- | --- | --- |
| Example 1 | Example Compound 2 | 1.4 |
| Example 2 | Example Compound 4 | 1.4 |
| Example 3 | Example Compound 6 | 1.6 |
| Example 4 | Example Compound 11 | 1.4 |
| Example 5 | Example Compound 19 | 1.5 |
| Comparative Example 1 | Comparative Compound C1 | 1 |
| Comparative Example 2 | Comparative Compound C2 | 1.1 |

Referring to the results in Table 1, the organic EL devices of Examples 1 to 5 exhibited higher emission efficiencies than Comparative Examples 1 and 2. The material for an organic EL device according to an embodiment of the present disclosure is an aniline derivative having a structure in which dibenzoheterole groups are bonded (e.g., coupled) to a phenyl group of a triarylamine at the ortho positions relative to the nitrogen atom. Accordingly, a conjugation system may not be increased (e.g., pi conjugation in the molecule may be limited), and an energy gap may not increase in the material (e.g., a small HOMO-LUMO gap may be maintained), and the emission efficiency of the organic EL device may be improved. Comparative Example 1 contains Comparative Compound C1, which contains phenyl groups at the ortho positions. The molecule is not substantially polar, and the emission efficiency is deteriorated or reduced when compared to that of Examples 1 to 5. Comparative Example 2 contains Comparative Compound C2, in which dibenzoheterole groups are introduced (e.g., coupled) at the meta positions. The molecule is not substantially polar, and the emission efficiency is deteriorated.

From the results in Table 1, the organic EL devices using the materials for an organic EL device of the present disclosure as hole transport materials were recognized to have higher efficiency when compared to those using the comparative compounds. Since the material for an organic EL device according to the present disclosure is an aniline derivative having a structure in which dibenzoheterole groups are bonded (e.g., coupled) to a phenyl group of a triarylamine at the ortho positions relative to the nitrogen atom, the polarity of the molecule may be increased due to the heteroatoms of the dibenzoheterole groups, and an energy gap (e.g., HOMO-LUMO gap) may be enlarged or increased due to the large steric distortion of the molecule around the amine group, thereby improving the emission efficiency of the organic EL device.

The material for an organic EL device according to an embodiment of the present disclosure may be an aniline derivative having a structure in which dibenzoheterole groups are introduced (e.g., coupled) to a phenyl group of a triarylamine at the ortho positions relative to the nitrogen atom. The polarity of the molecule may be increased due to the heteroatoms of the dibenzoheterole groups, and an energy gap (e.g., HOMO-LUMO gap) may be enlarged owing to the large steric distortion of the molecule around the amine group. Accordingly, a conjugation system may not be increased (e.g., pi conjugation in the molecule may be limited), and an energy gap (e.g., HOMO-LUMO gap) may be enlarged or increased. Thus, the emission efficiency of the organic EL device may be improved. In addition, since the material for an organic EL device has a wide energy gap, application of embodiments of the present disclosure to organic EL devices in the green and red emission regions may be possible.

In the present disclosure, an aniline derivative having a structure in which dibenzoheterole groups are introduced (e.g., coupled) to a phenyl group of a triarylamine at the ortho positions relative to the nitrogen atom. Accordingly, the polarity of the molecule may be increased due to the heteroatoms of the dibenzoheterole groups, and an energy gap (e.g., HOMO-LUMO gap) may be increased due to the large steric distortion of the molecule around the amine group. Therefore, a material for an organic EL device having high device efficiency and high emission efficiency, an organic EL device including the same, and a method of preparing the material may be provided.

As used herein, expressions such as "at least one of" and "one of", when preceding a list of elements, modify the entire list of elements and do not modify the individual elements of the list. Further, the use of "may" when describing embodiments of the present disclosure refers to "one or more embodiments of the present disclosure".

In addition, as used herein, the terms "use", "using", and "used" may be considered synonymous with the terms "utilize", "utilizing", and "utilized", respectively.

As used herein, the terms "substantially", "about", and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

The above-disclosed subject matter is to be considered illustrative and not restrictive, and the appended claims are intended to cover all such modifications, enhancements, and other embodiments, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. An organic electroluminescent (EL) device, comprising:
an anode;
an emission layer on the anode; and
a laminated layer between the anode and the emission layer,
wherein the laminated layer comprises a hole transport layer, and the hole transport layer comprises at least one of the following compounds:

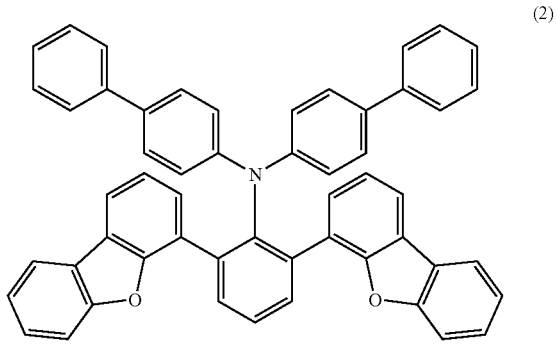

(2)

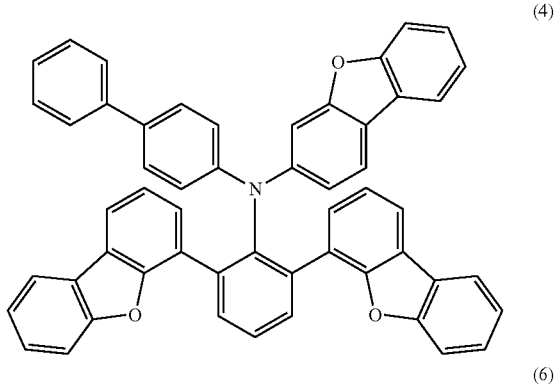

(4)

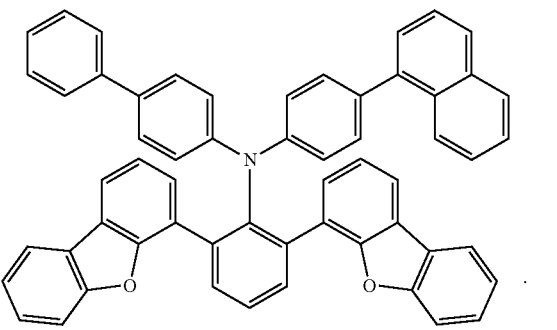

(6)

* * * * *